United States Patent [19]

Yoshikawa

[11] Patent Number: 5,043,430
[45] Date of Patent: Aug. 27, 1991

[54] PROCESS FOR TREATING INSOLUBLE HETEROLOGOUS PROTEIN

[75] Inventor: Kazuhide Yoshikawa, Yokohama, Japan

[73] Assignee: Tosoh Corporation, Shinnanyo, Japan

[21] Appl. No.: 335,798

[22] Filed: Apr. 10, 1989

[30] Foreign Application Priority Data

Apr. 8, 1988 [JP] Japan ................................ 63-85284

[51] Int. Cl.$^5$ ......................... C07K 3/24; C07K 15/12; C12N 15/18
[52] U.S. Cl. .................................... 530/399; 530/412; 530/419; 435/69.7
[58] Field of Search ............. 530/412, 419, 399, 69.7; 435/68, 69.7

[56] References Cited

FOREIGN PATENT DOCUMENTS 0114506 8/1984 European Pat. Off. .
0122080A1 10/1984 European Pat. Off. .

OTHER PUBLICATIONS

Greene et al., *Proc. Natl. Acad. Sci. USA,* "Establishment of a Noradrenergic Clonal Line of Rat Adrenal Pheochromocytoma Cells which Respond to Nerve Growth Factor", vol. 73, No. 7, pp. 2424-2428, Jul. 1976.

Biotechnology, vol. 7, pp. 1141-1149, Catherine H. Schein, "Production of Soluble Recombinant Proteins in Bacteria", Nov. 1989.

*Primary Examiner*—Margaret Moskowitz
*Assistant Examiner*—Keith L. Farman
*Attorney, Agent, or Firm*—Foley & Lardner

[57] ABSTRACT

A process for the solubilization of a protein obtained via heterologous expression comprises the step of bringing the insoluble protein produced in transformed host cells into contact with an aqueous acid solution in the presence of a protein denaturant. The process also preferably comprises the further steps of elevating the pH value of the solution, by addition of alkali substance, and thereafter lowering the pH to obtain a biologically-active protein.

7 Claims, No Drawings

PROCESS FOR TREATING INSOLUBLE HETEROLOGOUS PROTEIN

BACKGROUND OF THE INVENTION

The present invention relates to the solubilization, purification and refolding of proteins, especially fusion proteins, produced by genetically-transformed bacteria and other host organisms. In the following description, the expression product of such a transformed host is called a "heterologous protein," while a "fusion protein" is the product coded for by a DNA comprised of multiple peptide-encoding sequences that are translated as a single protein.

Proteins are known to be characterized by primary, secondary, tertiary and, sometimes, quaternary structures. The primary structure of a protein is made up of about 20 kinds of amino acids, and more than 200 different primary structures have so far been established. The so-called "higher order," secondary and tertiary structures of a protein are formed, for example, by hydrogen bonding, S-S bonding or hydrophobic bonding, between amino acids which make up the primary protein structure of that protein. More than 100 kinds of tertiary structures have been established as a result of X-ray diffraction analysis of protein crystal structure.

By means of various gene-manipulation techniques, it is possible to introduce DNA into a host organism in such a way that the host produces a foreign (heterologous) protein coded for by the introduced DNA. The heterologous protein thus produced often assumes a higher-order structure which inhibits physiological activity and causes the protein to remain, in the host cells, in the form of insoluble agglomerates. Effective utilization of such insoluble protein typically requires a series of treatments, including solubilization, purification and refolding.

There are several conventional treatments for solubilizing and refolding of insoluble protein produced in genetically-transformed host cells. For example, the insoluble protein may be solubilized in a solution containing a strong protein denaturant, such as a 4 to 9 M solution of guanidine hydrochloride, and then refolded by reducing the concentration of the protein denaturant. But this approach presents the problem of how to handle a large volume of solutions, because dialysis or dilution of the protein/denaturant solution is required to lower the concentration of the protein denaturant. When a compound like guanidine hydrochloride is used, an additional problem arises in handling the resulting waste liquid, since disposal of guanidine hydrochloride cannot be effected by any usual method for waste-liquid disposal, such as the active sludge method.

According to another process to accomplish refolding, insoluble heterologous protein is solubilized in an alkali solution and thereafter refolded by decreasing the pH of the solution. This process is simpler and easier to implement than the aforementioned approach employing a denaturant, and is more readily used in handling a large amount of materials, since the lowering of the pH can be achieved by adding an acidic substance.

One problem with the acidification method, however, is slow rate of solubilization of heterologous protein, due to the lack of contact of the alkali solution with the interior of the protein agglomerates. A slow rate of solubilization is undesirable because it causes a lower yield.

Also by virtue of recent advances in genemanipulation techniques, it is known that even those proteins, which are difficult to obtain via heterologous expression in transformed host cells, can be obtained as a component of a fusion protein which further comprises another protein segment more easily expressed in the host. According to this approach, two or more polypeptides are separated, as components of a fusion product, by an amino-acid sequence that is specifically digested by a proteolytic enzyme, such as thrombin, factor Xa or trypsin, so that the desired protein can be obtained when the fusion product is later digested by the enzyme.

For treatments such as solubilization, purification and refolding, there are usually optimum conditions for each heterologous protein, including a fusion protein, that result in the desired structure. For example, an insoluble fusion protein, as can be produced by suitably transformed *Escherichia coli*, that is comprised of the $\beta$-subunit of human nerve growth factor ("NGF") and at least a part, particularly an N-terminal portion, of the human growth hormone ("hGH") molecule, may be solubilized upon treatment with an alkali solution, but may precipitate when pH is lowered to effect refolding, occasioning a substantial decline in yield.

SUMMARY OF THE INVENTION

It is therefore an object of the present invention to provide treatments for solubilizing, purifying and refolding heterologous proteins, which treatments do not suffer the disadvantages of the conventional approaches discussed above.

It is also an object of the present invention to provide a process for treating insoluble heterologous protein, including a fusion protein obtained from genetically-engineered host cells, which is readily implemented and can accommodate large amounts of material without generating hard-to-handle waste liquids.

In accomplishing the foregoing objects, there has been provided, in accordance with one aspect of the present invention, a process for solubilizing an insoluble heterologous protein, comprising a step (a) of bringing insoluble protein produced by a genetically-transformed host organism into contact with an aqueous acid solution in the presence of a protein denaturant. In a preferred embodiment, the process of the present invention further comprises, after step (a), the step of isolating impurities, exclusive of the heterologous protein, from the solution. Thus, step (a) may be followed by a step (b) of elevating the pH of the aforementioned solution, by the addition to the solution of an alkali substance, such that impurities (but not the protein) are precipitated. In another preferred embodiment, the process also includes a step (c), after step (b), in which the pH of the solution is lowered such that the heterologous protein undergoes refolding into a biologically-active form.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

In accordance with a preferred embodiment of the present invention, an aqueous acid solution with a weak protein denaturant is brought into contact with a crude preparation of fragmented bacteria which includes insoluble, heterologous protein and which is prepared by breaking up transformed host cells, for example, by homogenization or by sonication. Alternatively, a concentrate of fragmented bacteria, prepared from such a crude preparation via centrifugation, ultrafiltration or gel filtration, is contacted with an aqueous acid solution in the presence of a protein denaturant. In either case, the protein is thereby solubilized.

A protein treated pursuant to the present invention can be combined, at the N-terminal end, with all or a part of an allogenic or heterogenic protein which is easily expressible by the host cells. As mentioned previously, an illustration of such a fusion protein is a protein comprising β-NGF and hGH (hereafter "NGF-hGH").

Protein denaturants which can be used in the present invention include commonly known denaturants like guanidine hydrochloride, urea, surfactants and thiocyanic acid salts. Among these, urea is the most preferred because it is the least reactive biologically (that is, in a living body) and is easily disposable. A suitable concentration for the protein denaturant is one at which an insoluble protein is readily dispersed in solution; the concentration necessary for such dispersion can be determined empirically, taking into account the nature of the denaturant employed. When urea is used as denaturant, for example, two considerations are that protein is generally denatured by urea at a concentration higher than 2 M and that agglomerates of insoluble protein may be dispersed at a concentration of urea lower than that at which protein is denatured. Therefore, a urea concentration of approximately 2 M is usually preferable.

Protein denaturants can be kept separately, in dissolved form or in an aqueous acid solution, or combined with the insoluble protein prior to the time that an aqueous acid solution is brought into contact with the protein agglomerates. The latter approach may be preferred to the extent that a lesser amount of the protein denaturant typically suffices.

In accordance with the present invention, dispersing the insoluble heterologous protein with a protein denaturant makes it easier for the acid solution to penetrate deep into the inner portion of the protein agglomerates, thus improving the rate of solubilization. During the dispersing and solubilizing operations, the whole mixture can also be agitated in order to facilitate these processes.

An aqueous acid solution used pursuant to the present invention can be an aqueous solution of any common acid substance selected, for instance, from inorganic acids such as hydrochloric acid, thiocyanic acid, hydroiodic acid and hydrobromic acid, or from an organic acid like acetic acid. Aqueous solutions of organic acids are preferred because organic acids are more effective in the denaturation of heterologous proteins. A suitable concentration of an acid substance employed in the present invention can be one that provides a pH, in aqueous solution, at which the desired heterologous protein is reversibly acid-denatured. For the above-mentioned NGF-hGH fusion protein, for example, a pH of 2 to 5, preferably 3 to 4, is appropriately achieved with an acid substance used according to the present invention.

After a solubilizing treatment is carried out as described above, the heterologous protein in solution can be purified by an appropriate conventional technique, such as ammonium sulfate precipitation or column chromatography. Alternatively, a purification step is preferably carried out, in accordance with the present lo invention, that entails increasing pH by the addition of an alkali substance to the acid solution which contains the solubilized protein. Alkali substances thus employed include, without restriction, sodium hydroxide, potassium hydroxide, sodium carbonate, ammonia, alkylamines and the like.

The pH is preferably elevated to a value where the heterologous protein is reversibly denatured by alkali and, more preferably, to as high a pH as possible. At a high pH value, impurities exclusive of the heterologous protein may precipitate, improving purification, and at the same time the ratio of solubilized protein to the total amount of starting protein in an aqueous alkali solution can be improved. In the case of a NGF-hGH fusion protein, the pH should be elevated to between about 10 and 13. Contaminants which precipitate at a high pH can be removed via any conventional technique which is suitable, such as by centrifugation, ultrafiltration, gel filtration and the like.

Refolding heterologous protein according to the present invention preferably follows the aforementioned purification step, and preferably involves a lowering of the pH of an aqueous alkali solution wherein the protein is dissolved, causing the protein to refold into a form that is capable of physiological activity. When a high concentration of protein denaturant is used in the solubilization treatment, as described above, an additional step of lowering the concentration of the denaturant is usually needed eventually, even for the enzymatic digestion of a fusion protein.

In a solubilization treatment involving refolding pursuant to the present invention, it is therefore preferable to effect dispersion of heterologous protein agglomerates either by using the protein denaturant at a concentration where the protein is not denatured or, alternatively, by using the denaturant at a high concentration that is lowered, when the solution is mixed with an aqueous acid solution, to a value insufficient to denature the protein. When a high concentration of a protein denaturant is used, and the resultant solution in which the refolding treatment is to be effected contains the denaturant at a concentration high enough to denature the fused protein, the concentration may be lowered, if necessary, by dialysis or dilution. The use of a protein denaturant in the solubilization treatment, of the present invention is advantageous in obtaining a higher rate of solubilizing insoluble heterologous protein and, therefore, in improving the final yield of the protein.

Pursuant to a preferred embodiment of the present invention, therefore, a heterologous protein is first solubilized in an aqueous acid solution, whereafter the pH of the solution is elevated by addition of an alkali substance. To this end, familiar alkali substances can be employed, as described above, in the purification treatment. Organic bases such as ammonia and triethylamine are especially useful because they typically provide a higher rate of refolding than do other alkali substances.

A higher rate of refolding can be also be achieved when an aqueous solution of at least one organic base is employed that is selected from the group consisting of monoethanolamine, diethylenetriamine, triethylenetetramine and tetraethylenepentamine. The mechanism for the higher refolding rate achieved with these organic bases is not clear, but their straight-chain structure may be a contributing factor in this regard.

As described above, the pH during purification should be elevated to a range in which the fused protein is reversibly denatured by alkali. For a NGF-hGH fusion protein, for example, a pH of less than 10 is insufficient for denaturation in an alkaline solution, while a pH greater than 13 can lead to irreversible denaturation. Accordingly, a pH in the range 10 to 13 is preferable. A pH in the range 11 to 12 is especially preferable in order to obtain a higher rate of refolding. Presumably, this is because the pH subtly influences refolding, as well as solubilization, in an alkaline medium.

In this manner, an alkaline solution can be obtained in which a heterologous protein is stably dissolved. For instance, a NGF-hGH fusion protein may be precipitated, if solubilized only with an aqueous alkaline solution, when the pH of the solution is lowered for refolding. But, by the operations described above, the protein is kept in solution without precipitating and, furthermore, impurities can be removed. The removal of impurities may be conducted at the stage where the pH is elevated, as explained above.

The lowering of pH can be carried out by dialysis and the like, but a more preferable approach, by virtue of the easiness in operation, is to add either an inorganic acid, such as hydrochloric acid or sulfuric acid, or an organic acid like acetic acid or glycine. As indicated above, however, dialysis of the solution is particularly useful when the solution, in which refolding is to be effected still contains denaturant in a concentration that is high enough to denature the heterologous protein and, therefore, lowering of the concentration is necessitated. Dialysis achieves a reduction of both pH and the concentration of denaturant simultaneously. The pH should be adjusted to a lower value compared with that of an alkaline solution. A preferable range is between 7 and 9, more preferably 7 to 8, ranging from neutral to weakly alkaline. In this range (neutral to weakly alkaline), heterologous proteins can exist and remain stable.

Before the pH of the alkaline solution is lowered, addition of a sulfhydryl compound, such as glutathione in the reduced form, cysteine, 2-mercaptoethanol, dithiothreitol, hydrogen sulfide and the like, is recommended in order to enhance disulfide-bond formation in the heterologous protein and, hence, to improve the rate of refolding.

The solubilization treatment of the present invention permits one to solubilize fusion proteins in a simple and easy operation. Also, the process for purification according to this invention makes it possible, in a readily implemented operation involving the addition of an alkali substance, to remove impurities contained in the acid solution comprising heterologous protein subjected to a solubilization treatment according to the present invention. In accordance with a refolding treatment of the present invention, moreover, the pH of an alkaline solution containing a heterologous fusion protein, which has been obtained via solubilization and purification treatments like those described above, is lowered to obtain the desired protein in a form displaying biological activity. These processes of the present invention are suited to rapid, convenient treatments, even for so large a quantity of heterologous protein that could not to be treated by conventional methods. In particular, when urea is used as protein denaturant, exhaust liquids could be disposed of in a simple operation.

The present invention is further described below by reference to the following illustrative examples, which relate to a NGF-hGH fusion protein produced by transformed E. coli. But the scope of this invention is not restricted to these examples.

The NGF-hGH protein of the examples has a molecular weight of about 30,000 daltons. The N-terminal region of the protein is part of the hGH molecule, comprising 140 amino acids, while the C-terminal region is part of the NGF molecule, comprising 118 amino acids. Since these two portions are separated after the refolding, they are joined via a specific recognition amino-acid sequence (Ile-Glu-Gly-Arg) which contains a cleavage site for a proteolytic enzyme (factor Xa). The NGF-hGH protein was obtained in the following examples from transformed E. coli host cells, according to the procedure described below after Comparison Z, this procedure being described in Japanese Laid-Open Patent application Sho No. 61-205485 and U.S. patent application Ser. No. 7/312,555, the respective contents of which are hereby incorporated by reference.

EXAMPLE 1

Solubilization of Heterologous Protein Upon Treatment with Acetic Acid and Urea

After culturing the transformed host cells, 10 g of the separated bacterial material were suspended in 100 ml of a 20 mM Tris-hydrochloric acid buffer solution (pH 8) containing 5% glycerol and 2 mM EDTA. The bacterial material was fractionated in an ultrasonic cell blender and was then centrifuged to precipitate the fusion protein. The NGF-hGH fusion protein was obtained as 8 g of precipitate which also included insoluble bacterial fragments. The precipitate was suspended in 200 ml of a 0.1 M aqueous acetic acid solution (pH 4) containing 7 M urea. This solubilization treatment resulted in the solubilization of the portion of the precipitate containing the fusion protein.

EXAMPLE 2

Purification Treatment

To the aqueous acetic acid solution containing the NGF-hGH solubilized in Example 200 ml of monoethanolamine solution (10% by volume) were added, and the pH was adjusted to 12. In the alkaline solution thus produced, protein other than the NGF-hGH, was precipitation, together with impurities which were not solubilized in Example 1. The precipitate thus formed was removed by centrifugation. The resulting supernatant contained the solubilized NGF-hGH, while the precipitate contained other proteins and impurities.

EXAMPLE 3

Obtaining Biologically Active Protein After Refolding Treatment

A 400 ml aliquot of the NGF-hGH-containing alkali supernatant obtained in Example 2 was dialyzed against 10 l of a 0.15 M Tris-hydrochloric acid buffer solution (pH 8.5), thereby to lower both the concentration of urea and the pH (to 8.5). No precipitation of protein was observed during this stage of dialysis. After the dialysis, a solution of crude protein containing 500 mg of NGF-hGH was obtained. To a solution containing 1 mg of crude extract of the NGF-hGH thus obtained were added 10 μg of factor Xa (product of Sigma Co.), and the mixture was treated at 37° C. for an hour, clearing the NGF from the hGH.

The solution after the treatment was submitted to the electrophoresis on SDS-polyacrylamide to analyze the protein composition. It was confirmed that there was present hGH with a molecular weight of about 15,000 daltons, and NGF with a molecular weight of about 14,000 daltons. Conversely, the presence of undigested NGF-hGH was not detected, an indication that adequate refolding of the fusion protein (and, hence, proper presentation of the enzyme recognition site for factor-Xa digestion) had been accomplished.

The crude NGF solution, containing NGF obtained as mentioned above, was added to a culture solution of rat pheochromocytoma PC12 cells, and an assay for NGF activity was conducted in accordance with Greene, *Proc. Nat'l Acad. Sci. USA* 73: 2424 (1976), the contents of which are hereby incorporated by reference. When the NGF solution was added to the culture medium so as to obtain a protein concentration of 1 μg/ml, the observed activity was of the same magnitude as that seen when a control mouse NGF ("NGF 2.5S," product No. 6009 of Sigma Co.) was added to provide 100 ng/ml. This fact confirmed that the NGF in the resultant solution had refolded to a state in which the NGF was physiologically active.

In this example and in others, the amount of protein in solution was determined by absorbance at 280 nm.

EXAMPLE 4

Treatments for Solubilization, Purification and Refolding (with Reduced Glutathione) to Obtain Active Heterologous Protein Pursuant to the same procedure followed in Examples 1 and 2, 10 g of a precipitate containing NGF-hGH from host cells were obtained. This precipitate was suspended in 200 ml of a 0.1 M aqueous acetic acid solution (pH 4) containing 3.5 M urea, and a solubilization treatment was conducted. Then 200 ml of monoethanolamine solution (10% by volume) were added and, after the pH was adjusted to 12, the whole mixture was centrifuged to remove the separated precipitate. Reduced glutathione was added to a concentration of 1 mM, the solution was agitated for 90 minutes, and the pH of the solution was adjusted to 8.5 by the addition of hydrochloric acid. The solution thus prepared contained 450 mg of protein and NGF that was found to be physiologically active, confirmed in the same manner as in Example 3.

Comparison 1

Treatment Without Addition of an Alkali Substance

A precipitate (8 g) obtained from host cells in the same manner as in Example 1 was solubilized with the use of 200 ml of an acetic acid solution (pH 4) containing 3.5 M of urea, the resulting solution was dialyzed against 10 l of a 0.15 M Tris-hydrochloric acid buffer solution (pH 8.5) without addition of an alkali substance. Most of the protein dissolved in the solution precipitated out. 50 mg of precipitate were obtained by centrifugation and suspended in the dialysis solution. An attempt to digest NGF and hGH with factor Xa was made but proved fruitless. Electrophoresis on SDS-polyacrylamide showed that most of the NGF-hGH remained undigested. Testing of this protein solution for NGF activity, as in Example 3, provided negative results. Thus, NGF produced in this manner was found to have no physiological activity.

Comparison 2

Treatment Without Contacting Insoluble Heterologous Protein with Acid Solution in the Presence of a Denaturant A precipitate (8 g) obtained from host cells in a manner similar to that in Example 1 was solubilized with 200 ml of a solution of monoethanolamine (10% by volume; pH 12) containing 3.5 M of urea. This solution was dialyzed against 10 l of a 0.15 M Tris-hydrochloric acid solution (pH 8.5). Then most of the protein dissolved in the solution precipitated out. The precipitate was treated in a manner similar to that described in Comparison 1, but no NGF activity was detected.

The NGF-hGH protein solubilized according to the present invention is obtained according to the procedure described below. Reagents mentioned in this description are designated as follows:

| | |
|---|---|
| Standard buffer solution | 50 mM Tris-Hydrochloric acid pH 7.5 |
| | 35 mM MgCl$_2$ |
| | 35 mM 2-Mercaptoethanol |
| Tris-NaCl | 10 mM Tris-Hydrochloric acid pH 8.0 |
| | 0.14 mM NaCl |
| TE-Sucrose | 25% (w/v) sucrose |
| | 50 mM Tris-Hydrochloric acid pH 8.0 |
| | 1 mM EDTA |
| Lysozyme | 10 mg/ml lysozyme |
| | 0.25M Tris-Hydrochloric acid pH 8.0 |
| 0.5M EDTA | pH 8.0 |
| RNase A | Dissolved in a 0.04M acetate buffer solution (pH 5.0) to a concentration 10 mg/ml, and heated at 100° C. for 5 minutes |
| Lytic mixture | 0.1% Non-ionic surfactant (Triton X-100) |
| | 50 mM Tris-Hydrochloric acid pH 8.0 |
| | 62.5 mM EDTA |
| Polyethyleneglycol (PEG) 6000 | Class 1 reagent in powder |
| 5M NaCl | |
| CsCl | Solid |
| EB solution | Prepared by dissolving ethidium bromide in water to 7 mg/ml |
| TE | 10 mM Tris-Hydrochloric acid pH 7.4 |
| | 1.0 mM EDTA |
| TE-Sarkosyl | 10 mM Tris-Hydrochloric acid |
| | 1 mM EDTA |
| | 0.38% Sodium N-Lauroyl Sarkosinate pH 7.4 |
| TEN | 10 mM Tris-Hydrochloric acid |
| | 1 mM EDTA |
| | 0.1M NaCl pH 7.4 |

Construction of Plasmid pNF-7:

The plasmid pNF-7, representing the starting material for the exemplified embodiment of the present invention, is synthesized according to the procedure described below, as disclosed in Japanese Laid-Open Patent Application No. Sho 61-205485, the contents of which are hereby incorporated by reference.

Synthesis of the oligonucleotide dGATCTTCATC-GAAGGTCGTTCCTCC(U$_{1-1}$) was carried out by the following procedure. 50 Milligrams of the 5'-(4,4'-dimethoxytrityl)-N-benzoyldeoxycytidine carrier (100 μmol/g of polystyrene resin) was kept overnight in pyridine at the room temperature, and then the condensation reaction was carried out by the following steps:

(1) washing, 3 times, with 2 ml of dichloromethane-methanol (7:3, V/V);

(2) treatment for 2 minutes with 2 ml of a 2% solution of benzenesulfonic acid in dichloromethanemethyl alcohol (7:3) followed by washing, three times, using the same mixture solution. The procedure is repeated until no more coloration is observed;

(3) washing, 3 times each, with 2 ml of pyridine;

(4) adding 0.2 ml of a solution of 5,-(4,4'-dimethoxytrityl)-thymidinyl-P-(o-chlorophenyl)-N-benzoyldeoxycytosine- 3'-(o-chlorophenyl)phosphate in pyridine (containing 20 mg of the nucleotide of the same) and then distillation under a reduced pressure to remove the solvent;

(5) as a condensation agent, a pyridine solution (0.2 ml) of mesitylenesulfonyl-3-nitrotriazolide (20 mg) was added and kept standing for 20 min at 40° C.;

(6) washing twice, respectively, with 2 ml of pyridine;

(7) addition of a 0.1 M solution (1.8 ml) of dimethylaminopyridine in pyridine and acetic anhydride (0.2 ml), followed by standing for 3 minutes; and (8) washing 3 times each with 2 ml of pyridine. The same procedures as in step (2) above were followed except that 5'-(4,4-dimethoxytrityl)-N-benzoyldeoxycytosinyl-P-(o-chlorophenyl) deoxycytosine-3'-(o-chlorophenyl) phosphate.

The DNA strand was further extended gradually in the 5' direction using dTT, dCG, dGT, dAG, dGA, dTC, dCA, dTT, dTC and dGA having similar protective groups. Then the resin was shaken for 38 hr in a 1 ml solution of 0.5 M trimethylguanidium-pyridine-2-aldoxymate, see Reese et al, *Tetrahedron Lett.* 2727 (1978), in dioxane-water (9:1). The resin was then washed with 50% aqueous pyridine and the washings were combined and concentrated under reduced pressure. Concentrated ammonia (15 ml) was added to the residue, the container tightly closed, and then warmed for 5 hr at 55° C. Ammonia was removed by distillation. Two milliliters of a pyridine-type strongly acidic cationic exchange resin (Dowex 50) was added, and then the resin was washed with 50% aqueous pyridine, and finally the liquid was combined with the concentrated washings. A small amount of water was added to the concentrate and the oxime was removed by extraction with ethyl acetate. The aqueous phase was diluted with water, and a portion was sampled to analyze for the total amount of dimethoxytrityl groups present. Assuming a molar absorption coefficient of dimethoxytrityl group to be 71,700, 1 μmol of crude oligonucleotide was found to have been synthesized from 77.4 $A_{254}$ units.

The aqueous phase was then heated to dryness under vacuum. The residue was treated with 10 ml of 80% acetic acid and the mixture was kept at 25° C. for 30 minutes. The solvent was removed by distillation and the residue was dissolved in a mixture of water and ethyl acetate. The aqueous phase was concentrated and treated by ion exchange chromatography, using a DEAE-Toyopearl 650S exchanger. A column (0.7×2cm) was packed with the resin and elution was conducted with a concentration gradient of 0.1 to 0.3 M sodium chloride in a 20mM TrisHCl buffer solution (pH 7.5). Oligonucleotide content was detected by ultraviolet absorption. A middle fraction of membrane for the purpose of desalting, to obtain 12.3 $A_{260}$ units, equal to 600 μg. A correspondence between the high performance liquid chromatography (HPLC), with a $C_{18}$ silica gel carrier, and the one-dimensional homo-chromatography confirmed the purity of the product.

Synthesis of the oligonucleotide dGTGAGAG-GAGGAACGACCTTCGATGAA($L_{1-1}$) was accomplished by the following procedure. The condensation reaction was carried out in the same manner as for $U_{1-1}$ (above) except for the variations of (1) using a 5'-(4,4-dimethoxytrityl) adenosine carrier, (2) starting with 5'-(4,4'-dimethoxytrityl)quanidyl-P-(o-chlorophenyl)-N-benzoyldeoxyadenine-3'-(o-chlorophenyl) phosphate and (3) the dinucleotides having protective groups were used in the amounts indicated by underlines in Table 1-2, and the extension of DNA strands, removal of the protective groups, and separation and purification of product were conducted as described above for the oligonucleotide $U_{1-1}$. Using the above procedure, it was possible to obtain 5.6 $A_{260}$ units (or 280 μg) of $L_{1-1}$.

In a similar procedure, the oligonucleotides that composed $U_{1-2}$, $U_{1-3}$, ... and $U_{1-23}$ and $L_{1-2}$, $L_{1-3}$, ... and $L_{2-23}$ (see Tables 2-1 and 2-2) were prepared, using 5'-(4,4'-dimethoxytrityl)-N-isobutyryldeoxyguanosine carrier, 5'-(4,4'-dimethoxytrityl)-N-benzoyldeoxyadenosine carrier, 5'(4,4-dimethoxytrityl)-N-benzoyldeoxycytidine carrier and 5'-(4,4-dimethoxytrityl)-thymidine carrier, mono- or dinucleotides having protective groups, respectively, that were successively condensed from the 3' end toward the 5' end in accordance with the base sequence indicated in Tables 2-1 and 2-2. The procedure was followed in the same manner as for $U_{1-1}$ and $L_{1-1}$, wherein the protective groups were removed and finally the products were separated and purified. The oligonucleotides obtained are shown in Tables 2-1 and 2-2.

TABLE 2-1

| $U_{1-1}$ | 5' GATCTTCATCGAAGGTCGTTCCTCC 3' |
|---|---|
| $U_{1-2}$ | 5' TCTCACCCGATCTTC 3' |
| $U_{1-3}$ | 5' CACCGTGGCGAATTC 3' |
| $U_{1-4}$ | 5' TCTGTTTGCGATTCC 3' |
| $U_{1-5}$ | 5' GTTTCTGTATGGGTT 3' |
| $U_{1-6}$ | 5' GGTGACAAAACCACT 3' |
| $U_{1-7}$ | 5' GCTACCGACATCAAAGG 3' |
| $U_{1-8}$ | 5' TAAAGAAGTAATGGTTC 3' |
| $U_{1-9}$ | 5' TGGGCGAAGTTAACATT 3' |
| $U_{1-10}$ | 5' AATAACTCCGTATTC 3' |
| $U_{1-11}$ | 5' AAGCAATATTTTTTT 3' |
| $U_{1-12}$ | 5' GAAACTAAATGCCGT 3' |
| $U_{1-13}$ | 5' GACCCGAACCCGGTT 3' |
| $U_{1-14}$ | 5' GACTCTGGTTGTCGTGG 3' |
| $U_{1-15}$ | 5' TATCGACTCCAAACACT 3' |
| $U_{1-16}$ | 5' GGAACTCTTACTGCACC 3' |
| $U_{1-17}$ | 5' ACTACCCACACCTTCGT 3' |
| $U_{1-18}$ | 5' GAAAGCTCTGACAATGG 3' |
| $U_{1-19}$ | 5' ATGGTAAACAGGCAGCT 3' |
| $U_{1-20}$ | 5' TGGCGTTTCATCCGCAT 3' |
| $U_{1-21}$ | 5' CGACACCGCTTGCGTAT 3' |
| $U_{1-22}$ | 5' GTGTTCTGTCTCGTAAG 3' and |
| $U_{1-23}$ | 5' GCTGTTCGTTAATAG 3' |

TABLE 2-2

| $L_{1-1}$ | 5' GTGAGAGGAGGAACGACCTTCGATGAA 3' |
|---|---|
| $L_{1-2}$ | 5' CCACGGTGGAAGATCGG 3' |
| $L_{1-3}$ | 5' CAAACAGAGAATTCG 3' |
| $L_{1-4}$ | 5' ACAGAAACGGAATCG 3' |
| $L_{1-5}$ | 5' TTGTCACCAACCCAT 3' |
| $L_{1-6}$ | 5' TCGGTAGCAGTGGTT 3' |
| $L_{1-7}$ | 5' TTCTTTACCTTTGATG 3' |
| $L_{1-8}$ | 5' TCGCCCAGAACCATTAC 3' |
| $L_{1-9}$ | 5' AGTTATTAATGTTAACT 3' |
| $L_{1-10}$ | 5' ATTGCTTGAATACGG 3' |
| $L_{1-11}$ | 5' TAGTTTCAAAAAAAT 3' |
| $L_{1-12}$ | 5' TCGGGTCACGGCAT 3' |
| $L_{1-13}$ | 5' CAGAGTCAACCGGGT 3' |
| $L_{1-14}$ | 5' GAGTCGATACCACGACAAC 3' |

TABLE 2-2-continued $L_{1-15}$ 5' AAGAGTTCCAGTGTTTG 3'
$L_{1-16}$ 5' GTGGGTAGTGGTGCAGT 3'
$L_{1-17}$ 5' AGAGCTTTCACGAAGGT 3'
$L_{1-18}$ 5' GTTTACCATCCATTGTC 3'
$L_{1-19}$ 5' GAAACGCCAAGCTGCCT 3'
$L_{1-20}$ 5' GGTGTCGATGCGGAT 3'
$L_{1-21}$ 5' AGAACACATACGCAAGC 3'
$L_{1-22}$ 5' GAACAGCCTTACGAGAC 3' and
$L_{1-23}$ 5' TCGACTATTAAC 3'

Synthesis of each of nerve growth factor gene fragments I, II, III, IV and V was carried out by the following procedures. Synthesis of nerve growth factor gene fragment I was carried out using the oligonucleotides $U_1$, $U_2$ and $U_3$ and $L_1$, $L_2$ and $L_3$ prepared in the syntheses of oligonucleotides above.

These oligonucleotides were combined with 0.25 microcurie [$\gamma$-$^{32}$P] ATP, representing 1 μl of a solution of the labelled ATP at a level of $1.2 \times 10$ cpm/μmol. An oligonucleotide with an OD 0.2 ($A_{260}$) was then combined with 0.5 μl of a $T_4$ polynucleotide kinase (prepared by Takara Shuzo Co., Ltd.) solution (6 u/μl) dissolved in 2 μl of the kination buffer solution (250 mM) of Tris-HCl (pH 8.0). Next, 50 mM of $MgCl_2$, 50 mM of 2-mercaptoethanol and 5 mM of spermine) were mixed and incubated for 20 min at 37° C. An additional 0.025 μl of 20 mM ATP was then added and allowed to react for 45 minutes. This was followed by addition of 1 μl of 20 mM ATP and then incubation for 45 minutes. A final addition of 10 mM Tris-HCl (pH 8.0) and 1 mM EDTA were made to obtain a reading of 10 $A_{260}$ or μl.

For annealing the fragments thus obtained, the reaction mixture was heated at 70° C. in 5 μl of the ligation buffer solution (330 mM Tris-HCl at pH 7.6, 33 mM $MgCl_2$ and 2.5 mM ATP) for 2 min, and then cooled gradually to room temperature. To the reaction mixture was added 1.3 μl of 2-mercaptoethanol (0.2 M 2-EtSH) and then the mixture was cooled to 13° C., followed by addition of 2 μl of $T_4$ DNA ligase (350 u/μl; prepared by Takara Shuzo Co., Ltd.) and an additional incubation for 2 hr. The resulting solution was then heated to 65° C. for 5 min to stop the reaction. The DNA fragments thus formed were extracted with phenol and precipitated with ethanol. The precipitate obtained was then separated by centrifugation, submitted to electrophoresis in a 10% polyacrylamide gel (150 V for 2.5 hr), extracted, and then precipitated again with ethanol. The precipitated DNA was then centrifuged and the DNA redissolved in a mixture of 10 mM Tris-HCl (pH 8.0) and 1 μM EDTA. Each DNA solution had an O.D. of at least 0.05 A260 unit (or 2.0 μg).

The fragments described below were thus obtained:

5' GATCTTCXTCCTCCTCTCACCCGATCTTCCACCGTGGC I:
AAGXAGGAGGAGAGTGGGCTAGAAGGTGGCACCG
GAATTC 3'
CTTAAGAGACAAAC

In a similar way, fragment II was obtained from $U_{1-4}$ to $U_{1-8}$ and from $L_{1-4}$ to $L_{1-8}$, fragment III from $U_{1-9}$ to $U_{1-13}$ and from $L_{1-9}$ to $L_{1-13}$, fragment IV from $U_{1-14}$ to $U_{1-18}$ and from $L_{1-14}$ to $L_{1-18}$ and fragment V from $U_{1-19}$ to $U_{1-23}$ and $L_{1-19}$ to $L_{1-23}$.

5' TCTGTTTGCGATTCCGTTTCTGTA                II:
CGTAAGGCAAAGACAT
TGGGTTGGTGACAAAACCACTGCTACCGAC
ACCCAACCACTGTTTTGGTGACGATGGCTG
ATCAAAGGTAAAGAAGTAATGGTTC 3'
TAGTTTCCATTTCTTCATTACCAAGACCCGCT

5' TGGGCGAAGTTAACATTAATAACTCCGTATTCAAG    III:
TCAATTGTAATTATTGAGGCATAAGTTC
GAAGTTAACATTAATAACTCCGTATTCAAG
CTTCAATTGTAATTATTGAGGCATAAGTTC
CCGAACCCGGTT 3'
GGCTTGGGCCAACTGAGAC

5' GACTCTGTTGTCGTGGT                        IV:
CAACAGCACCA
ATCGACTCCAAACACTGGAACTCTTACTGC
TAGCTGAGGTTTGTGACCTTGAGAATGACG
ACCACTACCCACACCTTCGTGAAAGCTCTG
TGGTGATGGGTGTGGAAGCACTTTCGAGAC
ACAATGG 3'
TGTTACCTACCATTTG

5' ATGGTAAACAGGCAGCTTGGCGT                  V:
TCCGTCGAACCGCA
TTCATCCGCATCGACACCGCTTGCGTATGT
AAGTAGGCGTAGCTGTGGCGAACGCATACA
GTTCTGTCTCGTAAGGCTGTTCGTTAATAG 3'
CAAGACAGAGCATTCCGACAAGCAATTATCAGCT

Total synthesis of nerve growth factor gene was achieved, through the use of the $T_4$.DNA ligase, from nerve growth factor gene fragments I, II, III, IV and V, which were prepared, as starting materials, via the respective syntheses described above and which were obtained as solutions in 10 nM Tris-HCl (pH 8.0) and 1 mM EDTA.

Each fragment in solution was provided in the amounts of 1 μl for I and 0.5 μl for II to V, respectively, and then diluted with 11.8 μl of water; heated in 4 μl of ligation buffer solution at 70° C. for two minutes; and then slowly cooled to the room temperature. Then 1 μl of 0.2 M 2-mercaptoethanol was added. After the reaction mixture was cooled to 20° C., 0.2 μl of a $T_4$ DNA ligase (350 u/μl; prepared by Takara Shuzo Co., Ltd.) was added and incubated for two hours. Heating to 65° C. for an additional five minutes was carried out before the reaction was stopped. After phenol extraction, the total synthesized nerve growth factor gene was precipitated with ethanol, separated by centrifugation, submitted to the electrophoresis on a 5% acrylamide gel, dissolved from the cut gel and precipitated again with ethanol.

The final preparation of the β-NGF gene containing plasmid was carried out as follows. Known plasmid ptrp ED5-1, see Hallewell & Emtage, Gene 9: 27 (1980), was digested with the restriction enzyme HinfI, to obtain HinfI-HinfI fragments consisting of about 500 base pairs each. Additionally, known plasmid pBR322, see Gene 2: 95 (1977), was digested with Eco RI. Both ends of the HinfI-HinfI fragments were made blunt ends by DNA polymerase in the presence of dNTP and digested with Eco RI, and inserted into the Eco RI cleavage sites of pBR322, to prepare the plasmid. Then the resulting plasmid was partially digested with Eco RI to cleave only at the Eco RI site, repaired with T4 DNA polymerase, and then adhesion was conducted with $T_4$ DNA ligase, to remove the Eco RI site. The resulting fragments were then digested twice with Eco RI and Bam HI to delete the region between the sites of Eco RI and Bam HI on the sequence originated from pBR322. The plasmid thus obtained was named "pOCT2-9," comprising 4.3 kilobases (Kb). Cloning was performed by transforming *E. coli* by Cohen's method, see Cohen et al, Proc. Nat'l Acad. Sci. U.S.A. 69: 2110 (1972), with Amp' and Tc$^s$ as markers.

The remaining Eco RI sites on the pOCT2-9 were then cleaved with Eco RI. Subsequently, exonuclease Bal 31 was employed to remove above 30 b.p. from both ends and a chemically synthesized linker Cla I,

```
5' AATCGATT 3'
  TTAGCTAA
``` was inserted into said removed portion with T$_4$ DNA ligase so as to form a closed ring, to obtain a plasmid, designated pCT1.

In the same manner as for pOCT2-9, the pCT1 obtained was transformed to *E. coli* for the purpose of cloning and multiplication. The sequence of plasmid pCT1, thus prepared, was ascertained by the method disclosed in Maxam & Gilbert, *Proc. Nat'l Acad. Sci. U.S.A.* 74:560 (1977). The plasmid pCT1 was doubly digested with Hpa I and Cla I, and a longer fragment was obtained by the polyacrylamide gel electrophoresis. The longer fragment was a fragment of pCT1 from which a ribosome attachment site in the trp leader region, an attenuator region and a ribosome attachment site of the primary structure gene, trp E, had been removed. To this fragment, a synthetic DNA segment represented as

```
                  5'
AAGTTCACGTAAAAAGGGTAATCGAT 3'
    TTCAAGTGCATTTTTCCCATTAGCTAGCC
``` was inserted and a closed ring form was made by adhesion with T$_4$ DNA ligase.

The plasmid thus obtained was cleaved with Cla I and Sal I and a longer fragment was obtained by the electrophoresis with polyacrylamide. Into this plasmid was inserted an hGH gene segment having the DNA sequence mentioned above and a Cla I restriction site at the 5' end (the positive strand) and a Sal I restriction site at the 3' end (the positive strand). The resulting construct was ligated into circular form with T$_4$ DNA ligase. In this manner, plasmid pGH-L9 was obtained, into which a suitable hGH-encoding sequence was integrated.

Plasmid pGH-L9 (*E. coli* pGH-L9; prepared from Micro Biotech. Inst. Bacteria Contr. No. 7606) in an amount of 5 μg was suspended in 6 μl of a standard buffer solution and digested at 37° C. for two hours with 12 u of Bgl II and 32 u of Sal I. The reaction mixture was treated by extraction with phenol, followed by precipitation with ethanol, to recover DNA. From this, DNA was extracted and separated by electrophoresis on 5% acrylamide gel to obtain about 3 μg of vector DNA pGH-L9/Bgl II-Sal I, which was linear, double-strand DNA. Three microliters of the resulting vector DNA pGH-L9/Bgl II-Sal I (0.5 μg/μl), containing a Bgl II site at its 5' end, were added to 3 μl of a kination mixture (0.3 μg/μl). To this mixture were added a β-NGF-encoding sequence, as described above, and a nucleotide sequence, encoding the amino-acid sequence Ile-Glu-Gly-Arg, that comprised a Sal I site its 3' end and a stop codon at its 5' end. The resulting mixture was combined with 8 μl of H$_2$O and allowed to react, at 20° C. for 20 hours, with 4 μl of a ligation buffer solution and 1 μl of 0.2 M of 2-mercaptoethanol in the presence of 1 μl of T$_4$-DNA ligase (350 u/μl).

After phenol extraction, the reaction mixture was mixed with ethanol to precipitate and recover DNA which was transformed and screened in the following procedure.

Recombinant plasmid PNF-7, at a concentration of 1.5 μg/20 μl (amount: 10 μl ), and *E. coli* HB101 were cultured overnight in 5 ml of L-broth, and again cultured in 100 μl until a absorbance of 0.15 A$_{660}$ was attained. Then the mixture was cooled on ice for 30 minutes, separated by centrifugation and the precipitate formed was suspended in 50 ml of 50 mM CaCl$_2$, and cooled on ice for 60 minutes, and separated by centrifugation. The resulting precipitate was mixed with 0.1 ml of calcium-treated bacteria suspended in 10 ml of 50 mM CaCl$_2$-20% glycerol; the whole mixture was kept at 0° C. and then heated to 42° C. for 60 seconds. The temperature was then allowed to return to the room temperature.

The mixture with 1 ml of L-broth (containing 1 g of Bacto-Tryptone, 0.5 g of Yeast Extract, 0.5 g of NaCl and 0.1 g of glucose, whole dissolved in 100 ml of water and adjusted to pH 7.2) was incubated for 30 to 60 minutes at 37° C. Centrifugation was applied at 13,000 rpm for 5 minutes, the supernatant liquid was discarded, and the precipitate was suspended in 0.3 ml of L-broth. Three portions, each 0.1 ml, were spread on separate agar media (3 mg of ampicillin was added to the medium consisting of 1 g of Bacto-Tryptone, 0.5 g of Yeast Extract, 0.5 g of NaCl and 0.1 g of glucose, and 1.5 g of agar). Those colonies were selected the plasmid fraction obtained from which gives an restriction enzyme cleavage map identical to that from pNF-7.

The bacteria multiplied in the agar media were suspended in STET buffer (consisting of 8% Sucrose, 50 mM Tris-HCl (pH 8.0). 50 mM EDTA and 5% Triton X 100). Twenty microliters of a lysozyme solution (containing 10 for 60 sec in boiling water and the centrifuged at 13,000 rpm for 10 minutes.

To the supernatant liquid, 0.5 ml of isopropanol was added and the mixture was let to stand for 30 minutes at −20° C. The precipitate formed by centrifugation at 13,000 rpm for 10 minutes was dissolved in 50 μl of a TE buffer solution, to which 80 μl of isopropanol were added and kept standing for 30 minutes at −20° C. Centrifugation at 13,000 rpm for 10 minutes formed a precipitate which was dried.

The precipitate was dissolved in 20.6 μl of H$_2$O, to which 6 μl of buffer, 0.9 ul of 5 M NaCl, 1 μl of Bgl II (8 u/μl) and 1.5 μl of Sal I (8 u/μl) were added, and the whole mixture was left to react at 37° C. for 90 minutes. Then 0.2 μl of RNase A (10 mg/ml) was added and allowed to react at 37° C. for 30 minutes.

The solution thus obtained was treated with phenol. The precipitate formed by addition of ethanol was separated by electrophoresis with 5% PAGE, to obtain a large amount of DNA which contained the β-NGF-encoding segment.

Synthesis of oligonucleotide (dGATCTTCGTTCCGCGTT)(U$_1$):

5'-(4,4'-Dimethoxytrityl)-N-benzoyldeoxythymidine carrier (50 mg of 100 μmol per gram of the polystyrene resin mentioned before) was kept standing overnight in pyridine at room temperature, and then underwent a condensation reaction in the following procedures:

(1) Washing 3 times each with 2 ml of dichloromethanemethanol (7:3, V/V).

(2) Treatment for 2 minutes with 2 ml of a 2% solution of benzenesulfonic acid (in a mixed solvent of dichloromethane and methylalcohol, 7:3), followed by washing three times with the same solvent to assure no coloration any more.

(3) Washing three times each with 2 ml of pyridine.

(4) Adding 0.2 ml of a solution of 5'-(4,4'-dimethoxytrityl)-guanidyl-P-(o-chlorophenyl)-N-benzoyldeoxythymidine- 3'-(o-chlorophenyl) phosphate in pyridine, containing 20 mg of nucleotide of said compound, and then distilling the solution under a reduced pressure.

(5) Adding 0.2 ml of a pyridine solution containing, as condensation agent, 20 mg of mesitylenesulfonyl-3-nitrotriazolide, and let standing at 40° C. for 20 minutes.

(6) Washing twice each with 2 ml of pyridine.

(7) Adding 1.8 ml of a 0.1 M solution of dimethylaminopyridine in pyridine and 0.2 ml of acetic anhydride and let standing for 3 minutes.

(8) Washing three times each with 2 ml of pyridine.

Then the same procedural steps (2) et seq. were followed, except with the modification of using 5'-(4,4-dimethoxytrityl)-N-benzoyldeoxyguanidyl-P-(o-chlorophenyl)deoxycytosine-3'-(o-chlorophenyl)phosphate in place of 5'-(4,4'-dimethoxytrityl)-guanidyl-P-(o-chlorophenyl)-N-benzoyldeoxythymidine-3'-(o-chlorophenyl)phosphate. The DNA strand was extended successively in the 5' direction by use of dCC, dTT, dCG, dTT, dTC and dGA having similar protective groups. Then the resin was immersed in 1 ml of a 0.5 M solution of trimethylguanidium-pyridine-2-aldoxymate in dioxane-water (9:1), C. B. Reese et al, *Tetrahedron Lett.* 2727 (1978), and the mixture was shaken for 38 hours.

The resin was washed with a 50% pyridine solution, and the liquid together with the washing were concentrated under a reduced pressure. The residue mixed with 15 ml of concentrated ammonia water was warmed in a sealed container at 55° C. for 5 hours. The ammonia was distilled out, 2 ml of a strongly acid pyridinium-type cation ion exchange resin (trade name "Dowex 50") were added, the resin was washed with a 50% pyridine solution, and the liquid together with the washing were concentrated. A small amount of water was added to the concentrate, and the oxime present in it was removed by extraction with ethyl acetate. The aqueous phase was diluted with water and a fraction was taken to quantitatively measure the dimethoxytrityl group for the estimation of the total amount. Based on a molar extinction coefficient of 71.700 for a dimethoxytrityl group, an observed $A_{254}$ value of 77.4 units indicated that 1 μmol of crude oligonucleotide was synthesized.

The aqueous phase was dried under a reduced pressure. The residue together with 10 ml of 80% acetic acid was kept at 25° C. for 30 minutes, and then the solvent was distilled out and the residue was dissolved in water and ethyl acetate. The water layer was concentrated and subjected to the ion exchange chromatography. DEAEToyopearl 650S (a trade name) was the ion exchanger used. This was placed in a column (0.7×21 cm) and eluted with a buffer solution of 7 M urea and 20 mM TRIS-hydrochloric acid (pH 7.5) under a concentration gradient of sodium chloride of 0.1 to 0.3 M. Oligonucleotide was detected by ultraviolet absorption measurement. The middle portion was taken and dialyzed to remove salt with a cellulose film, to obtain a product (500 μg) having a $A_{260}$ value of 10.0 units. The purity was ascertained by the HPLC (with a $C_{18}$ silica gel carrier) and the one-dimensional homochromatography giving a single component.

(2) Synthesis of dGAGGAACGCGGAACGAA ($L_1$)

The same procedure for the condensation reaction as in $U_1$ was followed except that a 5''-(4,4-dimethoxytrityl)-adenosine carrier and 5'-(4,4'-dimethoxytrityl)-quanidyl-P-(o-chlorophenyl)-N-benzoyldeoxyadenine-3'-(o-chlorophenyl)phosphate were employed at first.

Further employing the dinucleotides which comprised the base sequences according to those in Table 1-2 and protective groups for each, extension of the DNA strand, elimination of the protective groups and separation and purification of the product obtained were carried out in the same manner as in the case for $U_1$, to obtain 5.0 $A_{260}$ units (250 μg) of $L_1$.

In the similar manner, the oligonucleotides which compose $U_2$, $U_3$, $L_2$ and $L_3$ (see Tables 1-1 and 1-2) were prepared as described below:

A 5'-(4,4'-dimethoxytrityl)-N-butyryldeoxyguanosine carrier and a 5'-(4,4'-dimethoxytrityl)-N-benzoyldeoxyadenosine carrier were employed. The dinucleotides which comprised the base sequences according to those in Tables 1-1 and 1-2 and protective groups for each were condensed successively from the 3' end to the 5' end. Elimination of the protective groups and purification by separation were carried out for the preparation. The oligonucleotides thus prepared are shown in Tables 1-1 and 1-2.

TABLE 1-1

| $U_1$ | 5'GATCTTCGTTCCGCGTT 3' |
|---|---|
| $U_2$ | 5'CCTCCTCTCACCCGA 3' |
| $U_3$ | 5'TCTCCCACCGTGGCG 3' |

TABLE 1-2

| $L_1$ | 5'GAGGAACGCGGAACGAA 3' |
|---|---|
| $L_2$ | 5'AAGATCGGGTGAGAG 3' |
| $L_3$ | 5'AATTCGCCACGGTGG 3' |

Synthesis of DNA fragment I:

The synthesized DNA fragment I was prepared from the oligonucleotides $U_1$, $U_2$ and $U_3$ and $L_1$, $L_2$ and $L_3$ produced by the syntheses of oligonucleotides mentioned above.

A mixture of 1 μl of a solution containing 0.25 μCi of [γ-$^{=}$P] ATP (1.2×10 cpm/μl), OD 0.2 ($A_{260}$) of each oligonucleotide and 0.5 μl of a solution of polynucleotide kinase (produced by Takara Shuzo Co., Ltd.) containing 6 u/μl dissolved in 2 μl of a kination buffer solution [containing 250 mM of Tris-HCl pH 8.0, 50 mM of MgCl$_2$, 50 mM of 2-mercaptoethanol and 5 mM of spermine] was incubated at 37° C. for 20 minutes. Then 0.025 μl of 20 mM ATP was added and let to react for 45 minutes.

Further, 1 μl of 20 mM ATP was added to react for 45 minutes and then the solution was made 10 $A_{260}$/μ with added 10 mM Tris-HCl (pH 8.0) and 1 mM EDTA.

For annealing these fragments, the reaction mixture was heated at 70° C. for 2 minutes in a ligation buffer solution (containing 330 mM Tris-HCl pH 7.6, 33 mM of MgCl₂ and 2.5 mM of ATP) and then gradually cooled to the room temperature. The reaction mixture to which 1.3 μl of a 2-mercaptoethanol solution (02.M 2-EtSH) was added was cooled to 13° C., then mixed with 2 μl of T₄ DNA ligase (350 u/μl; prepared by Takara Shuzo Co., Ltd.) and incubated for 2 hours. After heating the mixture for 5 minutes at 65° C., the reaction was stopped. The DNA fragment formed was treated with phenol and mixed with ethanol. The precipitate thus formed was separated by centrifugation, treated by the electromigration through a 10% acrylic amide gel (150 V, 2.5 hours), extracted from the gel, precipitated from ethanol, separated by centrifugation and dissolved in a solution of 10 mM Tris-HCl (pH 8.0) and 1 μM EDTA.

Thus, 0.05 A260 unit (2.0 μg) of the fragment described below was obtained.

5'GATCTTCGTTCCGGCGTTCCTCCTCTCACCCGATCTTCCACCGTGGGG 3'   Fragment I.
   AAGCAAGGCGCAAGGAGGAGAGTGGGCTAGAAGGTGGCACCGCTTAA Preparation of recombinant plasmid and transformed strains:

Plasmid pNF-7 (*E. coli*/pNF-7, deposited at Fermentation Research Institute (FRI), Deposition No. FERM P-8132 of Mar. 8, 1985 (see FIG. 3) in an amount of 5 μg was suspended in 6 μl of a standard buffer solution and digested at 37° C. for 2 hours with 12 u of Bgl II and 10 u of EcoRI. The reaction solution was extracted with phenol, precipitated with ethanol to recover DNA, which was then submitted to electromigration in a 5% acrylamide gel, to extract a double-stranded DNA portion and to obtain vector DNA pNF-7/Bgl II-EcoR I which was a straight double-stranded DNA weighing about 3 μg. A 3 μl volume of vector DNA pNF-7/Bgl II-EcoR I (0.5 μg/μl) and 3 μ of a kination mixture solution (0.3 μg/μl) of the DNA fragment I synthesized in Example 2 (having a Bgl II site at the 5' end, a succeeding base sequence Val-Pro-Arg of an amino acid codon, a portion of the hNGF gene and a end of the EcoRI site) were mixed with 8 μl of H₂O, 4 μl of a ligation buffer solution and 1 μl of 0.2 M solution of 2-mercaptoethanol. The whole mixture was reacted in the presence of 1 μl of T₄-DNA ligase (350 u/μl) for 20 hours at a temperature of 20° C.

After treating with phenol, DNA was recovered by precipitation with ethanol from the reaction mixture. Transformation and screening followed in the succeeding step of operation.

Ten microliters of the plasmid were obtained by the above operation. Then the culture was repeated using 100 μl of the fresh liquid. When 0.15 A₆₆₀ was reached, this was ice cooled for 30 minutes. A precipitate obtained by centrifugation was suspended in 50 ml of 50 mM CaCl₂ and ice-cooled for 60 minutes. The matter obtained by centrifugation was mixed with 0.1 ml of a calcium-treated bacterium which was suspended in a 10 ml solution of 50 mM CaCl₂-20% glycerol. This was maintained at 0° C., then heated at 42° C. for 60 seconds and returned to the room temperature. To this was added 1 ml of L-broth (1 g of Bacto-Tryptone, 0.5 g of Yeast Extract, 0.5 g of NaCl and 0.1 g of glucose dissolved in 100 ml of water and adjusted to pH 7.2), and the mixture was incubated for 30 to 60 minutes at 37° C. Then followed centrifugation at 13,000 rpm for 5 minutes. Supernatant liquid was removed and the precipitate formed was suspended in 0.3 ml of L-broth. Each 0.1 ml of the liquid was spread on an agar medium (prepared by adding 1.5 g of agar and 3 mg of ampicillin to a mixture of I g of Bacto-Tryptone, 0.5 g of Yeast Extract, 0.5 g of NaCl and 0.1 g of glucose). Those colonies were selected in which the restriction-enzyme cleavage map of the plasmid fraction obtained from each colony agreed with that of the anticipated plasmid, designated as pNF-T1, as shown in FIG. 4. This plasmid contains a DNA sequence coding for β-NGF and a DNA sequence coding for the amino-acid sequence of Val-Pro-Arg at the 5' side of DNA coding for a polypeptide comprised of the alpha and beta subunits of human growth hormone, hGH (A,B).

The bacteria grown in the agar medium were suspended in a STET buffer containing 8% sucrose, 50 mM Tris-HCl (pH 8.0), 50 mM EDTA and 5% Triton X-I00. To this, 20 μl of a lysozyme solution (containing 10 mg lysozyme per ml of 0.25 M Tris-HCl (pH 8.0)) were added, heated in a boiling water for 60 seconds and then subjected to centrifugation at 13,000 rpm for 10 minutes.

To the supernatant liquid, 0.5 ml of isopropanol was added and the mixture left to stand at −20° C. for 30 minutes, followed by centrifugation for 10 minutes at 13,000 rpm. The precipitate which formed was dissolved in 50 μl of a TE buffer solution; this, mixed with 80 μl of isopropanol, was kept standing at −20° C. for 30 minutes and then subject to centrifugation at 13,000 rpm for 10 minutes. The precipitate thus formed was dried.

The precipitate was dissolved in 20.6 μl of H₂O, to which were added 6 μl of the buffer, 0.9 μl of 5 M NaCl, 1 μl of Bgl II (8 u/μl) and 1.5 μl of Sal I (8 u/μl), and the mixture was let to react at 37° C. for 90 minutes. Then this was mixed with 0.2 μl of RNase A (10 mg/ml) and let to react at 37° C. for 30 minutes.

The solution obtained was treated with phenol, precipitated with ethanol, then treated by electrophoresis with 5% PAGE, to obtain a large amount of the DNA aimed at which contained the β-NGF polynucleotide molecule.

Expression of β-NGF:

*E. coli*/pNF-T1, which produces β-NGF fused protein as obtained in Example 3, was cultured overnight in 5 ml of the culture medium indicated below.

| Na₂HPO₄ | 0.55 g |
|---|---|
| KH₂PO₄ | 0.2 g |
| NaCl | 0.5 g |
| NH₄Cl | 0.1 g |
| Casamino acid | 0.2 g |
| Glucose | 0.4 g |
| MgSO₄ | 0.1 mmol |
| CaCl₂ | 0.01 mmol |
| Thiamin-HCl | 1 mg |
| Ampicillin | 2 mg (per 100 ml medium) |

A 100 μl portion of the culture solution obtained above was first cultured in a 5 ml medium consisting of 0.2% of MgCl₂, 0.4% of casamino acid, glucose-ampicillin (20 μg/ml) and thiamin (10 μg/ml) for an hour, then 20 μl of 3-indolacrylic acid (10 mg/ml ethanol) was added to the medium and the culture continued for additional 24 hours.

After the culturing, bacteria were collected by centrifugation carried out at 13,000 rpm for 5 minutes.

A portion of the bacteria was suspended in 62.5 ml of a sample buffer Tris-HCl (pH 6.8) containing 2% of SDS 5 mM EDTA, 10% of glycerol, 35 mM 2-mercaptoethanol and 0.001% BPB, heated for 5 minutes in boiling water and then separated by centrifugation. Electrophoresis on 0.1% SDS-15% PAGE was carried out with the supernatant liquid to obtain a matter having a molecular weight $3.0 \times 10^4$. The pattern was scanned with a densitometer. The amount of formation was calculated. As a result, formation of the hGH-$\beta$-NGF fused protein was estimated to amount to 15% of the total protein.

What is claimed is:

1. A process for solubilizing a fusion protein produced by a genetically-transformed host organism, said fusion protein comprising, in the N-terminal region thereof, the amino acid sequence of human growth hormone linked via a first peptide bond to an amino acid sequence Ile-Glu-Gly-Arg which is linked via a second peptide bond to the amino acid sequence of a $\beta$-subunit of human nerve growth factor, said process comprising the steps of (a) bringing said fusion protein into contact with an aqueous acid solution in the presence of a protein denaturant for a time sufficient to solubilize said fusion protein and than (b) adding an alkali substance to said solution containing a protein denaturant to elevate the pH of said solution between about 10 to about 13, exclusive of said fusion protein, impurities precipitate from said solution.

2. A process according to claim 1, further comprising a step (c) of lowering the pH of said solution such that said fusion protein undergoes refolding into a biologically-active form.

3. A process according to claim 1, wherein said fusion protein is an expression product of genetically-transformed E. coli cells.

4. A process according to claim 1, wherein said protein denaturant comprises urea.

5. A process according to claim 1, wherein said alkali substance comprises at least one organic base selected from the group consisting of monoethanolamine, diethylenetriamine, triethylenetetramine and tetraethylenepentamine.

6. A process according to claim 2, wherein said alkali substance comprises at least one organic base selected from the group consisting of monoethanolamine, diethylenetriamine, triethylenetetramine and tetraethylenepentamine.

7. A process according to claim 2, wherein said pH of said solution is lowered in the presence of a sulfhydryl compound.

* * * * *